United States Patent
Paul et al.

(10) Patent No.: US 8,560,246 B2
(45) Date of Patent: Oct. 15, 2013

(54) METHOD FOR ADJUSTING RESULTS OF A POLYMERASE CHAIN REACTION (PCR) INSTRUMENT

(75) Inventors: Justin M. Paul, Raleigh, NC (US); Burton D. Beames, Raleigh, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 494 days.

(21) Appl. No.: 12/742,801

(22) PCT Filed: Nov. 11, 2008

(86) PCT No.: PCT/US2008/083113
§ 371 (c)(1),
(2), (4) Date: Sep. 14, 2010

(87) PCT Pub. No.: WO2009/064717
PCT Pub. Date: May 22, 2009

(65) Prior Publication Data
US 2011/0004411 A1    Jan. 6, 2011

Related U.S. Application Data

(60) Provisional application No. 60/987,895, filed on Nov. 14, 2007.

(51) Int. Cl.
*C12P 19/34* (2006.01)
*C12Q 1/68* (2006.01)
*C12Q 2537/165* (2006.01)
*C12Q 2561/113* (2006.01)

(52) U.S. Cl.
USPC ............... 702/19; 435/6; 435/6.16; 435/91.2

(58) Field of Classification Search
None
See application file for complete search history.

(56) References Cited

U.S. PATENT DOCUMENTS 6,387,621 B1 * 5/2002 Wittwer ...................... 435/6.16
7,228,237 B2 * 6/2007 Woo et al. ....................... 702/19

FOREIGN PATENT DOCUMENTS

WO    WO 02/00938 A2    1/2002
WO    WO 2006-014464 A2    2/2006

OTHER PUBLICATIONS

Kurnick, R. T. "Rotation algorithm for determining cycle threshold in real-time polymerase chain reactions." IEEE, Aug. 2007.*
Data Analysis on the ABI Prism 7700 Sequence Detection System: Setting Baselines and Thresholds (hereinafter "Setting Baselines"; see attached, 2002; as evidenced by User Bulletin #2, Oct. 2001).*
Guide to Performing Relative Quantitation of Gene Expression Using Real-Time Quantitative PCR (hereinafter "Performing qPCR"; see attached, 2004).*
Heid et al, (Real time quantitative PCR, Genome Res., 6: 986-994, 1996).*
Pfaffl (Relative Quantitation, in Real-Time PCR, Ed. T. Dorak, Taylor & Francis, New York, 2006, pp. 63-82).*
Pitfalls of Quantitative Real-Time Reverse-Transcription Chain Reaction, Journal of Biomolecular Techniques, vol. 15, Issue 3, Sep. 2004.*
Wong et al., Real-time PCR for mRNA quantitation, BioTechniques, 39:75-85, Jul. 2005.*
Bustin et al. (Absolute quantification of mRNA using real-time reverse transcription polymerase chain reaction assays, Journal of Molecular Endocrinology (2000) 25, 169-193).*
Meijerink, J., et al., "A Novel Method to Compensate for Different Amplification Efficiencies between Patient DNA Samples in Quantitative Real-Time PCR," *Journal of Molecular Diagnostics*, 3(2): 55-61 (2001).
Buller, R.S., et al., "Evaluation of a real-time PCR assay using the LightCycler system for detection of parvovirus B19 DNA," *Journal of Clinical Microbiology*, 42(7): 3326-3328 (2004).
Kurnik, R.T., "Rotation algorithm for determining cycle thresholds in real-time polymerase chain reactions," *IEEE* 1997-1980 (2007).
Barratt & Mackay "Improving Real-Time PCR Genotyping Assays by Asymmetric Amplification," J. Clin. Microbiol. 40(4):1571-1572 (2002).
Szilvási et al., "Asymmetric PCR increases efficiency of melting peak analysis on the LightCycler," Clin. Biochem. 38(8):727-730 (2005).
Weimer et al., "High-titer screening PCR: a successful strategy for reducing the parvovirus B19 load in plasma pools for fractionation," Transfusion 41(12): 1500-1504 (2001).

* cited by examiner

*Primary Examiner* — Christopher M Babic
*Assistant Examiner* — Aaron Priest
(74) *Attorney, Agent, or Firm* — Womble Carlyle Sandridge & Rice, LLP

(57) ABSTRACT

Methods of managing results of a real-time polymerase chain reaction (PCR) instrument and software associated with such methods are described herein. One disclosed method, among others, comprises calculating, from results of the real-time PCR instrument, a fluorescence signal of a sample during a cycle of a baseline period of the real-time PCR instrument. The method further comprises determining whether or not the fluorescence signal during the baseline period increases by at least a certain percentage compared to cycles outside the baseline period. The sample is flagged as a potentially high-titer sample when the fluorescence signal increases by at least the certain percentage.

10 Claims, 2 Drawing Sheets

METHOD FOR ADJUSTING RESULTS OF A POLYMERASE CHAIN REACTION (PCR) INSTRUMENT

CROSS REFERENCE TO RELATED APPLICATIONS

The present application is a U.S. national phase application of PCT/US08/83113 filed Nov. 11, 2008, which claims priority under 35 USC §119 to U.S. Provisional Application No. 60/987,895 filed Nov. 14, 2007, the entire contents of each of which are herein incorporated by reference in their entirety.

TECHNICAL FIELD

The present disclosure generally relates to polymerase chain reaction (PCR) instruments. More particularly, the disclosure relates to methods for verifying or adjusting results of sequence detection software (SDS) used in PCR instruments.

BACKGROUND

Real-time polymerase chain reaction (PCR) systems are used for amplifying a sample, such as a DNA strand, in order to make it easier to detect or identify the sequence of the sample. Real-time PCR devices use sequence detection software (SDS) for analyzing and processing the results of PCR tests. In some cases, however, the SDS is not able to accurately detect samples, which can result in improper identification of the existence or concentration of certain sequences. For example, when a sample of plasma blood is analyzed using certain Applied Biosystems PCR systems, or other systems using related SDS, the systems at times can fail to detect a high concentration of a virus, such as, for example, parvovirus B19. Consequently, the current systems can misinterpret a plasma sample containing a high titer of these viruses that would corrupt a pool of plasma, causing a significant loss of plasma resources.

Thus, a need exists in the current state of the art to address these and other deficiencies and inadequacies of the conventional systems and methods. Improvements to the conventional systems and methods, as described herein, are able to overcome these and other shortcomings of the prior art.

SUMMARY

The present disclosure describes methods for managing the results of a real-time polymerase chain reaction (PCR) instrument. According to one embodiment among many, a method disclosed herein comprises calculating, from results of the real-time PCR instrument, a fluorescence signal of a sample during a cycle of a baseline period of the real-time PCR instrument. The method also includes determining whether or not the fluorescence signal during the baseline period increases by at least a certain percentage compared to cycles outside the baseline period. Also, the method includes flagging the sample as a potentially high-titer sample when the fluorescence signal increases by at least the certain percentage.

According to another embodiment, a method is described for testing a blood sample and comprises quantifying viral nucleic acid in the blood sample using a real-time polymerase chain reaction (rtPCR) instrument by modifying the interpretation of data so that high titer samples are not misinterpreted. A fluorescence signal is calculated from PCR results provided during a baseline period. Also, it is determined whether the fluorescence signal increases by at least a predetermined percentage during the baseline period. The method also includes flagging the blood sample as a potentially high-titer sample when the fluorescence signal increases by at least the predetermined percentage.

The present disclosure also describes computer software or firmware, computer programs, software code sequences, and the like, embodied in a computer-readable medium and executable by a processing device. According to one embodiment, a software code sequence comprises logic configured to calculate a fluorescence signal of a sample during a baseline period of test cycles of a polymerase chain reaction (PCR) instrument. The software code sequence also includes logic configured to determine whether or not the fluorescence signal during the baseline period increases by at least a certain percentage compared to cycles outside the baseline period. Also, the software code sequence includes logic configured to flag the sample as a potentially high-titer sample when the fluorescence signal increases by at least the certain percentage.

Other features, advantages, and implementations of the present disclosure, not expressly disclosed herein, will be apparent to one of ordinary skill in the art upon examination of the following detailed description and accompanying drawings. It is intended that such implied implementations of the present disclosure be included herein.

DETAILED DESCRIPTION

Figure 1:
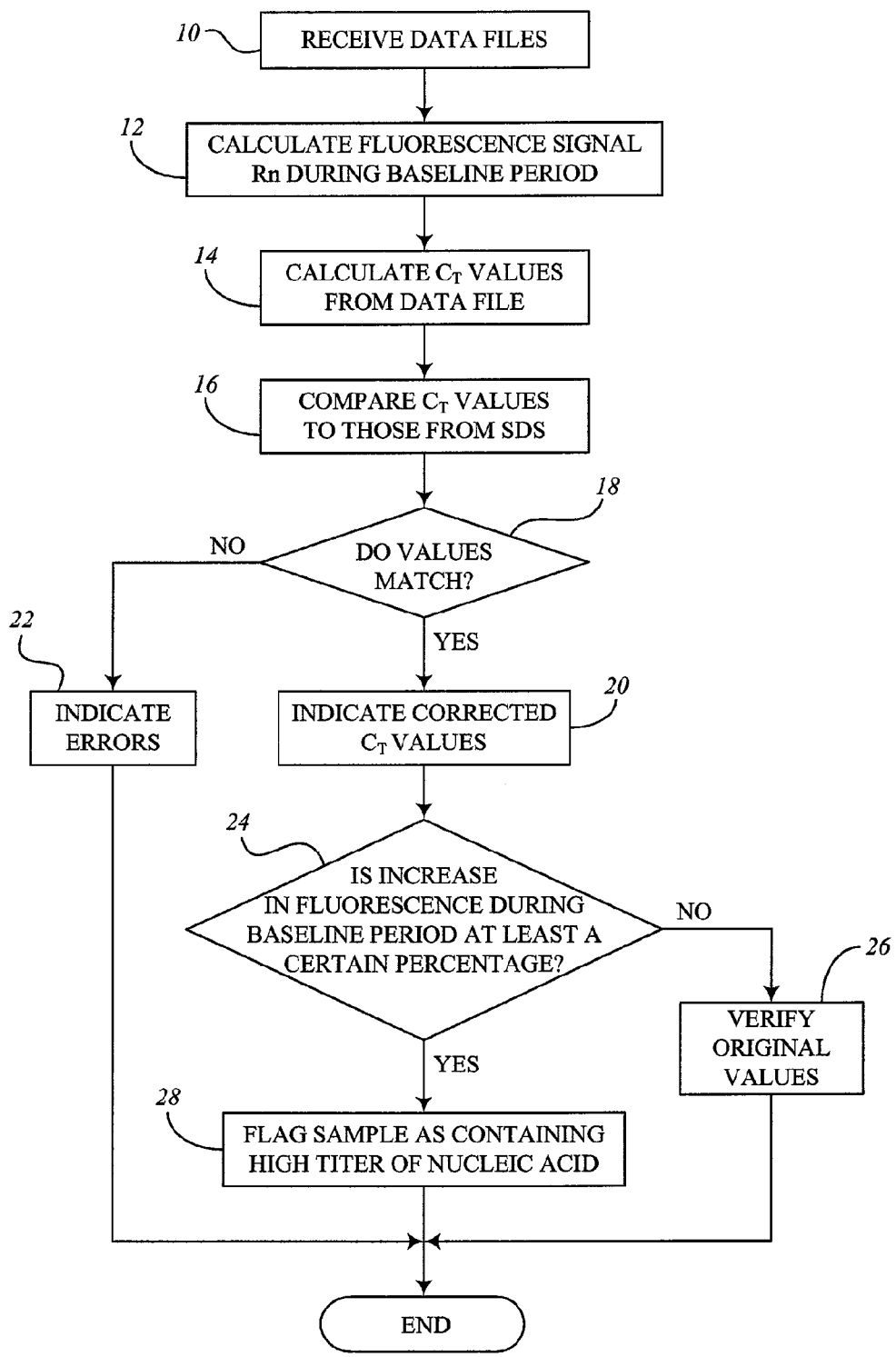
FIG. 1 is a flow chart describing a process for adjusting data results from a PCR device according to one embodiment.

Devices/Systems currently used to process and interpret polymerase chain reaction (PCR) data can incorrectly identify the concentration of some nucleic acids in the samples. This problem can be caused by how the results of the PCR tests are processed in sequence detection software (SDS) associated with the PCR analysis. For example, a number of PCR systems, such as many of the Applied Biosystems Real-Time PCR systems, utilize SDS that can fail to accurately detect samples of blood plasma containing high concentrations of viruses, e.g., parvovirus B19. Because of the way fluorescence is detected, it is possible that a blood plasma sample containing high virus titers could be overlooked as being clean. Particularly, it has been observed that fluorescence levels during a baseline period are elevated such that when fluorescence levels of the sample are compared to the baseline levels, there appears to be no significant increase above a threshold level to indicate a concentration of a virus. Therefore, a modification is required to overcome the software deficiencies and override the errant results to properly identify the concentration of a virus, if any, in a plasma sample.

The present disclosure describes methods of detecting high concentrations of nucleic acid that are amplified using conventional PCR instruments. Nucleic acids can be detected, for example, using a fluorogenic probe, such as a TaqMan® probe. In the presence of the target nucleic acid sequence, the probe is hydrolyzed during each PCR cycle and an increase in fluorescence is measured. The SDS can use an algorithm to separate the fluorescence into component wavelengths specific to the fluorescent dyes. Early PCR cycles, e.g., cycles 3 to 15, can be specifically set by a user to establish values from which a baseline fluorescence level is determined. The user also defines a threshold value assigned for each cycle that reflects a certain level of fluorescence greater than the calculated baseline level. The threshold cycle ($C_T$) indicates the PCR cycle number during which the fluorescence generated within a reaction exceeds the threshold and also indicates the detection of nucleic acid. However, it should be noted that samples with high concentration of nucleic acids tend to amplify during the baseline period. Thus, the SDS of some conventional PCR systems reads this fluorescence as background and incorrectly interprets these high concentration samples negative for target nucleic acid, when in actuality there may be a high concentration of the target sequence. The methods of the present disclosure compensate for these inaccurate results to provide a more accurate output, if necessary, or to verify the accuracy of the prior results.

The logic described herein overcomes at least two of the flaws in the SDS of conventional systems. First, the flawed SDS is unable to appropriately detect samples containing high-titer samples of nucleic acids, which are typically amplified during the baseline period. Because a large percentage of amplification occurs during the baseline period, an increase in fluorescence of a sample is compared against a threshold level that has been improperly raised above the elevated baseline level. As a result, the flawed SDS incorrectly identifies the sample as negative. The second flaw in the conventional SDS systems is that the data file, which contains the fluorescent data for detecting an increase, does not contain embedded identifying information. As a result of this, a data file could be incorrectly matched with a different sample. Thus, any comparisons using the data file would not be match with the correct set of results.

In one aspect of the present invention, the fluorescent data is analyzed to see if at least a certain percentage increase has occurred in the normalized fluorescence over the baseline. Results having an increase that does not exceed this certain percentage may be considered as being acceptable. As an example, the percentage may be set at about 20%, such that any sample that exhibits an increase of 20% or more is flagged as a potentially high-titer sample. Also, the $C_T$ values are calculated from the results and compared to those values originally calculated by the SDS. A discrepancy between the calculations indicates a potential error in the pairing of the data file with its results or could indicate an instrumentation error.

The PCR system typically takes fluorescence readings at each PCR cycle for each test sample. A component file stores the fluorescence readings separated into the component fluorescent dyes—FAM, JOE, and ROX—at each PCR cycle, where FAM and JOE are reporter dyes and ROX is a passive reference dye. In this example, the viral target is parvovirus B19. FAM would represent the viral target and JOE would represent the internal control (IC) target.

An algorithm, according to one implementation, involves calculating a normalized reporter signal (Rn). The Rn at each cycle c is calculated as the reporter dye fluorescence divided by the passive reference dye fluorescence. For the viral target:

$$Rn(V)_c = \frac{FAM_c}{ROX_c} \qquad \text{eqn. 1}$$

and for internal control (IC) target:

$$Rn(IC)_c = \frac{JOE_c}{ROX_c}. \qquad \text{eqn. 2}$$

Any sample generating an increase of at least 20% in viral target Rn(V) from PCR cycle 3 to cycle 15 is flagged as a potentially high-titer sample. If this is the case, then the algorithm uses the following equations to calculate the $C_T$ values. First, however, the baseline fluorescence is calculated using the linear regression of Rn over the baseline, which is defined as 3 to 15 for the viral target and 3 to 27 for the IC target. For the viral target:
the slope $$m_{FAM} = \frac{\sum_{c=3}^{c=15}(c-\overline{c})(Rn(V)_c - \overline{Rn(V)_c})}{\sum_{c=3}^{c=15}(c-\overline{c})^2} \qquad \text{eqn. 3}$$

and the intercept $$b_{FAM} = \overline{Rn(V)_c} - (m_{FAM} \times \overline{c}). \qquad \text{eqn. 4}$$

For the IC Target:
the slope $$m_{JOE} = \frac{\sum_{C=27}^{C=27}(c-\overline{c})(Rn(IC)_c - \overline{Rn(IC)_c})}{\sum_{c=3}^{c=27}(c-\overline{c})^2} \qquad \text{eqn. 5}$$

and the intercept $$b_{JOE} = \overline{Rn(IC)_c} - (m_{JOE} \times \overline{c}) \qquad \text{eqn. 6}$$

where $\overline{x}$ represents the average of x over the range of the baseline.

Then, the delta Rn (dRn) is calculated as the difference of the Rn and baseline fluorescence at each cycle. For the viral target:

$$dRn(V)_c = Rn(V)_c - (m_{FAM} \times c) - b_{FAM} \qquad \text{eqn. 7}$$

and for the IC target:

$$dRn(IC)_c = Rn(IC)_c - (m_{JOE} \times c) - b_{JOE}. \qquad \text{eqn. 8}$$

The algorithm then calculates the slope and intercept of dRn between each cycle, beginning at cycle 2. For the previous cycle of the viral target,
the slope $$m(V)_c = \frac{dRn(V)_c - dRn(V)_{c-1}}{c - (c-1)} \qquad \text{eqn. 9}$$

and the intercept $$b(V)_c = dRn(V)_c - (m(V)_c \times c). \qquad \text{eqn. 10}$$

For the previous cycle of the IC target, the slope $$m(IC)_c = \frac{dRn(IC)_c - dRn(IC)_{c-1}}{c - (c-1)} \qquad \text{eqn. 11}$$

and the intercept $$b(IC)_c = dRn(IC)_c - (m(IC)_c \times c). \qquad \text{eqn. 12}$$

The cycle threshold $C_T$ is calculated as the fractional cycle at which the dRn crosses a threshold value. For example, the threshold value for the viral target could be 0.1 and the threshold value for the IC target could be 0.02. For the viral target, if $dRn(V)_c > 0.1$ and $dRn(V)_{c-1} < 0.1$: then $$C_T(V) = \frac{0.1 - b(V)_c}{m(V)_c}. \qquad \text{eqn. 13}$$

For the IC target, if $dRn(IC)_c > 0.02$ and $dRn(IC)_{c-1} < 0.02$, then $$C_T(IC) = \frac{0.02 - b(IC)_c}{m(IC)_c}. \qquad \text{eqn. 14}$$

The calculated $C_T$ values are rounded to two decimal places and then compared to the values from the PCR results. The comparison is used to determine whether or not the component file is correctly paired with its results file and thus originate from the same assay run.

FIG. 1 is a flow chart illustrating an embodiment of a method for managing results of conventional SDS. The method of FIG. 1 is able to overcome the deficiencies of the faulty SDS results. The method includes receiving data files, as indicated in block 10. The data files can be received, for example, from SDS of a PCR system or from other processing and/or data storage systems associated with PCR analysis. In block 12, a fluorescent signal Rn is calculated during a baseline period, which, for example, may include cycles 3 to 15 of the PCR test. In some embodiments, the fluorescence signal Rn can be a normalized reporter signal of each cycle calculated by dividing the fluorescence of a reporter dye by the fluorescence of a passive reference dye.

In block 14, the threshold cycle ($C_T$) values are calculated from the data files. As described in more detail below, FIG. 2 includes a process for implementing this calculation of $C_T$ according to one embodiment. In block 16, the $C_T$ values calculated in block 14 are compared to the $C_T$ values received directly from the SDS. In decision block 18, it is determined whether or not the values compared in block 16 match, thereby ensuring the correct identity of the sets of results. If the values match, then the flow is directed to block 20. In block 20, an indication is made that the $C_T$ values have been corrected and the newly calculated $C_T$ values are verified as being reliable. If the values do not match, then the flow is directed to block 22, at which an indication is presented to the user that an error has occurred. The error could be the result of improper pairing of the newly calculated $C_T$ values and the $C_T$ values calculated by the SDS. The error could also be the result of an error in the instrumentation. After indication of the error in block 26, the flowchart ends.

In decision block 24, it is determined whether or not the fluorescence during the baseline period increases by at least a certain percentage, e.g., 20%, compared to the fluorescence during cycles outside the baseline period. If not, then it is determined that the sample does not contain a high titer of nucleic acid. In this case, the process includes verifying that the original values of the results of the PCR test are substantially accurate, as indicated in block 26, since the original values would not have been compared to elevated levels. When the original values are verified in block 26, the routine comes to a finish. However, if it is determined in decision block 24 that the fluorescence increase is at least the certain percentage, then the sample can be flagged as containing a high titer of nucleic acid, as indicated in block 28.

Figure 2:
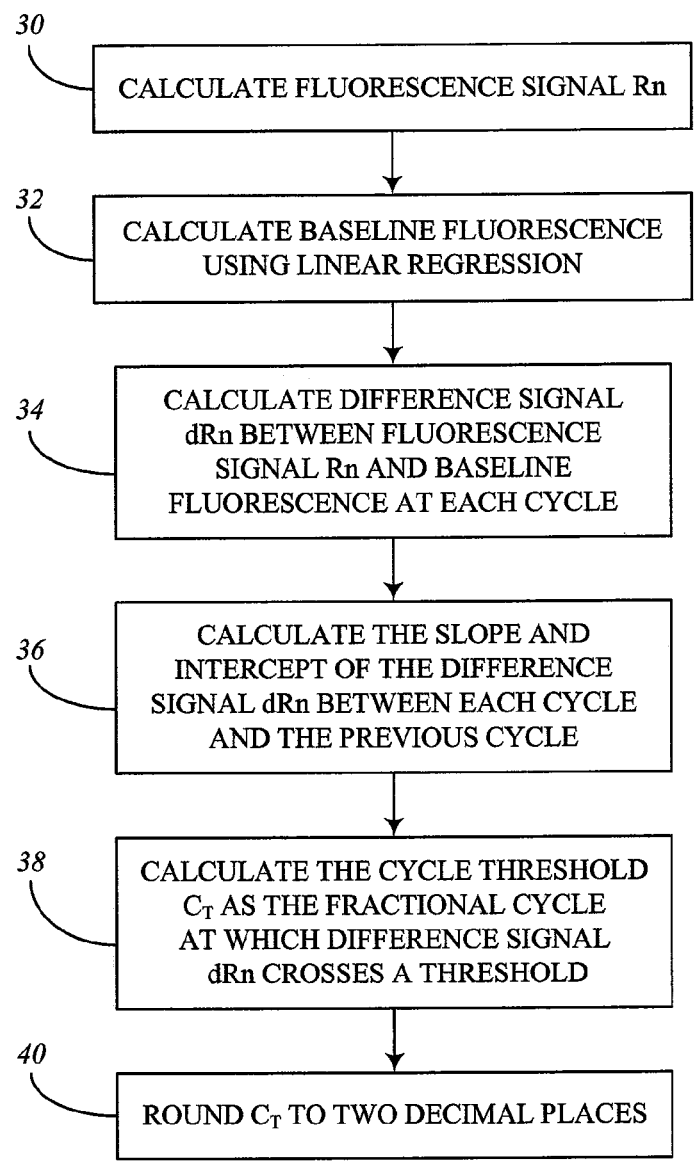
FIG. 2 is a flow chart describing a process for calculating threshold cycle according to one embodiment.

FIG. 2 is a flow chart illustrating an embodiment of a method for calculating $C_T$. The method of FIG. 2 can be used, for instance, in place of block 14 shown in FIG. 1 in which $C_T$ is calculated. In this method, block 30 indicates that a fluorescence signal Rn is calculated. In some embodiments, Rn is calculated by FAM/ROX. In block 32, a baseline fluorescence is calculated using a linear regression method. In alternative embodiments, other statistical methods may be used to calculate the baseline fluorescence. In block 34, a difference signal dRn is calculated in which dRn is the difference between the fluorescence signal Rn and the baseline fluorescence at each cycle. In block 36, a calculation is made of the slope and intercept of the difference signal dRn between each cycle and the previous cycle. In block 38, the cycle threshold $C_T$ is calculated as the fractional cycle at which difference signal dRn crosses a threshold. In block 40, $C_T$ is rounded to two decimal places.

The operations of the methods and processes described herein could be incorporated into one or more software programs and used to process the corrections and/or adjustments described herein and to generate an output of more accurate results compared with originally calculated results from traditional SDS. Such software programs could be used to replace a section of software code in any related SDS or developed into the SDS itself. The software programs could be used in SDS existing today or that which may be developed in the future. Also, the software program can be incorporated in any PCR analysis system that utilizes a similar processing format for analyzing a sample. In some embodiments, the software program could be incorporated in a stand-alone device and connected to an output of a conventional PCR system that provides the potentially faulty results as described above.

In addition to the presently disclosed methods being used to correct the output of the SDS, the method could also provide an indication of any corrections made. In this way, the methods could be used to provide the more accurate results after processing the signals as disclosed. Software logic for correcting or adjusting the signals could be stored on a computer-readable medium. In some embodiments, the methods and operations could be implemented in hardware or software and incorporated into a data management system, such as a laboratory information management system (LIMS), and/or incorporated into a spectrometer, such as an infrared interferometer spectrometer (IRIS).

It should be understood that the steps, processes, or operations of the methods described herein may represent any module or code sequence that can be implemented in hardware, software, firmware, or a combination thereof. When implemented in software or firmware, the methods can be stored in memory and executed by a processing device. When implemented in hardware, the methods can be implemented, for example, using discrete logic circuitry, an application specific integrated circuit (ASIC), a programmable gate array (PGA), a field programmable gate array (FPGA), etc., or any combination thereof. These modules and code sequences can include commands or instructions for executing specific logical steps, processes, or operations within physical components.

It should further be understood that one or more of the steps, processes, and/or operations described herein may be executed substantially simultaneously or in a different order than explicitly described, as would be understood by one of ordinary skill in the art. The programs or software code that include executable logical instructions, as described herein, can be embodied in any suitable computer-readable medium for execution by any suitable processing device. The computer-readable medium can include any physical medium that can store the programs or software code for a measurable length of time.

The embodiments described herein merely represent exemplary implementations and are not intended to necessarily limit the present disclosure to any specific examples. Instead, various modifications can be made to these embodiments as would be understood by one of ordinary skill in the art. Any such modifications are intended to be included within the spirit and scope of the present disclosure and protected by the following claims.

We claim:

1. An automated method for simultaneously managing results from a real-time polymerase chain reaction (PCR) instrument for the identification of samples comprising high-titer nucleic acids, the method comprising:
    (a) obtaining fluorescence data from sequence detection software (SDS) associated with a real-time PCR instrument;
    (b) independently calculating, from the data obtained from the SDS associated with the real-time PCR instrument, a normalized fluorescence signal ($R_n$) of a sample during a baseline period of the real-time PCR, wherein the baseline period is from about cycle 3 to about cycle 15;
    (c) determining whether the normalized fluorescence signal ($R_n$) increases by at least about 20% during the baseline period;
    (d) flagging the sample as a potentially high-titer sample when the normalized fluorescence signal ($R_n$) increases by at least about 20% during the baseline period;
    (e) comparing the SDS-calculated fluorescence data obtained from the SDS associated with the real-time PCR instrument to the independently calculated normalized fluorescence signal ($R_n$) of step (b) and
    (f) verifying that the SDS-calculated fluorescence data are substantially accurate.

2. The method of claim 1, further comprising:
    (g) independently calculating a threshold cycle ($C_T$) value from the fluorescence data from the SDS associated with the real-time PCR instrument; and
    (h) comparing the independently-calculated $C_T$ value to the SDS-calculated $C_T$ value to determine if there is a match.

3. The method of claim 2, further comprising:
    (i) indicating the SDS-calculated $C_T$ value as correct when there is a match; and
    (j) indicating the occurrence of an error when there is not a match.

4. The method of claim 2, wherein independently calculating a $C_T$ value comprises:
    (i) calculating a normalized fluorescence signal ($R_n$) as a ratio of FAM/ROX;
    (ii) calculating baseline fluorescence using a linear regression method;
    (iii) calculating a difference signal between the normalized fluorescence signal ($R_n$) and the baseline fluorescence at each cycle;
    (iv) calculating the slope and intercept of the difference signal between each cycle and the previous cycle; and
    (v) calculating the $C_T$ value as the fractional cycle at which the difference signal crosses a threshold.

5. An automated method for simultaneously testing blood or plasma for the identification of samples comprising high-titer nucleic acids, the method comprising:
    (a) analyzing a blood or plasma sample using a real-time polymerase chain reaction (PCR) instrument to provide PCR results;
    (b) obtaining fluorescence data from sequence detection software (SDS) associated with a real-time PCR instrument;
    (c) independently calculating, from the data obtained from the SDS associated with the real-time PCR instrument, a normalized fluorescence signal ($R_n$) of a sample during a baseline period, wherein the baseline period is from about cycle 3 to about cycle 15;
    (d) determining whether the normalized fluorescence signal ($R_n$) increases by at least about 20% during the baseline period;
    (e) flagging the blood or plasma sample as a potentially high-titer sample when the normalized fluorescence signal ($R_n$) increases by at least about 20% during the baseline period;
    (f) comparing the SDS-calculated fluorescence data obtained from the SDS associated with the real-time PCR instrument to the independently calculated normalized fluorescence signal ($R_n$) of step (c); and
    (g) verifying that the SDS-calculated fluorescence data are substantially accurate.

6. The method of claim 5, further comprising:
    (h) independently calculating a threshold cycle ($C_T$) value from the fluorescence data from the SDS associated with the real-time PCR instrument; and
    (i) comparing the independently-calculated $C_T$ value to the SDS-calculated $C_T$ value to determine if there is a match.

7. The method of claim 6, further comprising:
    (j) indicating the SDS-calculated $C_T$ value as correct when there is a match; and
    (k) indicating the occurrence of an error when there is not a match.

8. The method of claim 6, wherein independently calculating a $C_T$ value comprises:
    (i) calculating a normalized fluorescence signal ($R_n$);
    (ii) calculating a baseline fluorescence using a linear regression method;
    (iii) calculating a difference signal between the normalized fluorescence signal ($R_n$) and baseline fluorescence at each cycle;
    (iv) calculating the slope and intercept of the difference signal between each cycle and the previous cycle; and
    (v) calculating the $C_T$ value as the fractional cycle at which the difference signal crosses a threshold.

9. The method of claim 1, wherein the number of samples is greater than about 24.

10. The method of claim 5, wherein the number of samples is greater than about 24.

* * * * *